US008460917B2

(12) United States Patent
Brøndstad et al.

(10) Patent No.: US 8,460,917 B2
(45) Date of Patent: Jun. 11, 2013

(54) LACTOBACILLUS STRAINS

(75) Inventors: Gunnar Brøndstad, Snåsa (NO); Erik Brandsborg, Holbæk (DK)

(73) Assignee: Bifodan A/S, Hundested (DK)

( * ) Notice: Subject to any disclaimer, the term of this patent is extended or adjusted under 35 U.S.C. 154(b) by 1382 days.

(21) Appl. No.: 10/508,324

(22) PCT Filed: Mar. 21, 2003

(86) PCT No.: PCT/DK03/00195
§ 371 (c)(1),
(2), (4) Date: Jun. 10, 2005

(87) PCT Pub. No.: WO03/080813
PCT Pub. Date: Oct. 2, 2003

(65) Prior Publication Data
US 2005/0220776 A1 Oct. 6, 2005

Related U.S. Application Data

(60) Provisional application No. 60/366,847, filed on Mar. 21, 2002.

(30) Foreign Application Priority Data

Mar. 21, 2002 (DK) .................................. 2002 00435

(51) Int. Cl.
*C12N 1/20* (2006.01)
(52) U.S. Cl.
USPC ........................................................ 435/252.9
(58) Field of Classification Search
USPC ........................................................ 435/252.9
See application file for complete search history.

(56) References Cited

U.S. PATENT DOCUMENTS

| | | | | |
|---|---|---|---|---|
| 4,211,769 | A | * | 7/1980 | Okada et al. .................... 514/15 |
| 5,032,399 | A | | 7/1991 | Gorbach et al. |
| 5,466,463 | A | * | 11/1995 | Ford .............................. 424/433 |
| 5,645,830 | A | | 7/1997 | Reid et al. |
| 5,804,179 | A | | 9/1998 | Bruce et al. |
| 6,093,394 | A | | 7/2000 | Chrisope |
| 2002/0044926 | A1 | | 4/2002 | Reid et al. |

FOREIGN PATENT DOCUMENTS

| | | |
|---|---|---|
| EP | 956 858 | 11/1999 |
| EP | 1 034 787 A1 | 9/2000 |
| EP | 1 034 788 A1 | 9/2000 |
| WO | WO 92/13577 | 8/1992 |
| WO | WO 95/33046 | 12/1995 |
| WO | WO 97/29762 | 8/1997 |
| WO | WO 98/23727 | 6/1998 |
| WO | WO 98/46261 | * 10/1998 |
| WO | WO 99/29833 | 6/1999 |
| WO | WO 99/45099 | 9/1999 |

OTHER PUBLICATIONS

McLean et al. "Characterisation and selection of a *Lactobacillus* species to re-colonise the vagina of women with recurrent bacterial vaginosis" J. Med. Microbiol. vol. 49 (2000) p. 543.*
Boris et al. "Adherence of Human Vaginal *Lactobacilli* to Vaginal Epithelial Cells and Interaction with Uropathogens" Infection and Immunity,May 1998, p. 1985-1989.*
Rosenstein "Bacterial Vaginosis and the Normal Vaginal Flora: A Dynamic Relationship" Clin. Lab. 1998; 44; 949-960.*
Virginia S. Ocaiia, Elena Bru,'Aida A. P. de Ruiz H~Igado, and Maria Elena Nader-macias "Surface characteristics of *lactobacilli* isolated from human vagina" J. Gen. Appl. Michrobiol. 45, 2003-212 (1999).*
Answers.com, Definitions for Xanthan Gum and Alginate Accessed via www.answers.com Sep. 13, 2008.*
Gregor Reid et al., "The Role of *Lactobacilli* in Preventing Urogenital and Intestinal Infections," Int. Dairy Journal 8 (1998), 555-562.
Jane R. Schwebke, MD, "Role of Vaginal Flora as a Barrier to HIV Acquisition," Current Infectious Disease Reports 2001, 3:152-155.
G. W. Elmer, Probiotics: "living drugs," Am. J. Health Syst. Pharm. 2001, 58(12):1101.
J. R. Schwebke MD, "Role of Vaginal Flora as a Barrier to HIV Acquisition," Curr. Infect. Dis. Rep, Apr. 2001, 3(2):152-155 (Abstract.
P. Moodley et al., "Interrelationships among Human Immunodeficiency Virus Type 1 Infection, Bacterial Vagiosis, Trichomoniasis, and the Presence of Yeasts," J. Infect. Dis., Jan. 2002, 185(1)69-73.
C. N. Jacobsen et al., "Screening of Probiotic Activities of Forty-Seven Strains of *Lactobacillus* spp. by In Vitro Techniques and Evaluation of the Colonization Ability of Five Selected Strains in Humans," App. Environ. Microbio., Nov. 1999, 65(11): 4949-4956.
Reid et al., "The Role of *Lactobacilli* in Preventing Urogenital and Intestinal Infections,"Int. Dairy Journal, vol. 8, Issues 5-6, May 6, 1988, 8:555-562 (Abstract).
N. W. McLean, "Characterization and selection of a *Lactobacillus* species to re-colonise the vagina of women with recurrent bacterial vaginosis," J. Med. Microbiol., vol. 49 2000, pp. 543-552.
V. Ocana et al., "Adhesion of *Lactobacillus* Vaginal Strains with Probiotic Properties to Vaginal Epithelial Cells," Biocell, 2001, 25(3):265-273.
Antonio et al. "The Identification of Vaginal *Lactobacillus* Species and the Demographic and Microbiologic Characteristics of Women Colonized by These Species," *J. Infect. Dis*. 180:1950-56 (1999).
Burton et al., "Improved Understanding of the Bacterial Vaginal Microbiota of Women before and after Probiotic Instillation," *App. Environmen. Microbiol*. 69:97-101 (2003).
*Lactic acid Bacteria*. 3rd ed., Salminen et al., eds, Marcel Dekker, Inc, New York. Basel pp. 459-478 (2004).

(Continued)

*Primary Examiner* — Jon P Weber
*Assistant Examiner* — Thane Underdahl
(74) *Attorney, Agent, or Firm* — Finnegan Henderson Farabow Garrett & Dunner LLP (57) ABSTRACT

Novel Lactobacilli strains, *Lactobacillus acidophilus* strain Lba EB01 (Lba EB01), *Lactobacillus paracasei* strain Lbp PB01 (Lbp PB01), *Lactobacillus acidophilus* strain Lba EB02, *Lactobacillus plantarum* strain Lbpl PB02, *Lactobacillus* strain Lbxx EB03 and *Lactobacillus* strain Lbxx PB03, and strains with essentially the same advantageous properties which alone or in combination can be used as probiotics or together with a prebiotic as a synbiotic. The invention also relates to pharmaceutical compositions, dairy products, functional foods, nutraceutical and products for personal care comprising the strains alone or in combination, as well as use of the strain for prevention or treatment of vaginal infections, urogenital infections and gastrointestinal diseases.

13 Claims, 3 Drawing Sheets

OTHER PUBLICATIONS

Larsen, "Vaginal Flora in Health and Disease," *Clin. Obestet. Gynecol.* 36:107-21 (1993).

Ocaña et al., "Adhesion of *Lactobacillus* Vaginal Strains with Probiotic Properties to Vaginal Epithelial Cells," *Biocell* 25:265-73 (2001).

Ocaña et al., "Selection of Vaginal $H_2O_2$-Generating *Lactobacillus* Species for Probiotic Use," *Curr. Microbiol.* 38:279-84 (1999).

Reid et al., "Urogenital Infections in Women: Can Probiotics Help?" *Postgrad. Med. J.* 79:428-32 (2003).

Reid et al., "Effect of nutrient composition on the in vitro growth of urogenital *lactobacilli* and uropathogens," Can. J. Microbiol., 44(9): 866-871 (1998).

International Preliminary Examination Report for International Application No. PCT/DK03/00195, completed Aug. 18, 2004 (12 pages).

International Search Report for International Application No. PCT/DK03/00195, mailed Oct. 28, 2003 (4 pages).

* cited by examiner

Figure 1

Adherence of probiotic strains to cultured Caco-2 cells

LACTOBACILLUS STRAINS

CROSS REFERENCE TO RELATED APPLICATIONS

This application is a U.S. national phase application based on PCT/DK03/00195, filed Mar. 21, 2003, claims the priority of Danish patent application No. PA 2002 00435, filed on Mar. 21, 2002, and claims the benefit of U.S. Provisional Application No. 60/366,847, filed Mar. 21, 2002, the content of all of which is incorporated herein by reference.

FIELD OF THE INVENTION

The present invention relates to novel Lactobacilli strains, which alone or in combination can be used as probiotics or together with a prebiotic as a synbiotic. The invention also relates to pharmaceutical compositions, dairy products, functional foods, nutraceutical and products for personal care comprising the strains alone or in combination, as well as use of the strain for prevention or treatment of vaginal infections, urogenital infections and gastrointestinal diseases.

BACKGROUND OF THE INVENTION

Probiotics are live microorganisms or microbial mixtures administered to improve the patient's microbial balance, particularly the environment of the gastrointestinal tract and the vagina. Lactobacilli strains have been employed for the treatment of vaginal infections, prevention of diarrhea as well as for the treatment of urinary-tract infections (Am. J. Health Syst. Pharm. 2001, 58 (12): p 1101-1109).

The normal vaginal flora is dominated by *Lactobacillus* species, which produce substances that help control the growth of pathogens. Bacterial vaginosis (BV) is a clinical condition that is characterized by a decrease of the *Lactobacillus* species and an increased growth of anaerobic and mycoplasma bacteria. Bacterial vaginosis has been associated with the development of pelvic inflammatory disease and preterm labour. Some studies have suggested that patients with bacterial vaginosis may have an increased risk of contracting sexually transmitted diseases (STDs), including human immunodeficiency virus (HIV) infection (Curr Infect Dis Rep 2001 April; 3 (2) 152-155; J Infect Dis 2002 Jan. 1; 185 (1): 69-73).

By administering probiotic Lactobacilli, it is possible to regenerate the vaginal flora of women with recurrent episodes of bacterial vaginosis. Bacterial vaginosis is one of the most common female gynecological problems.

Vaginal infection caused by *Candida albicans* is also a common female gynecological problem.

The presence of Lactobacilli is important for the maintenance of the intestinal microbial ecosystem. Lactobacilli have been shown to possess inhibitory activity toward the growth of pathogenic bacteria such as *Listeria monocytogenes*, *Escherichia coli*, *Salmonella* spp and others. This inhibition could be due to the production of inhibitory compounds such as organic acids, hydrogen peroxide, bacteriocins or reuterin or to competitive adhesion to the epithelium (App. Environ. Microbiol., 1999, 65 (11) p 4949-4956).

Lactobacilli have also been examined as a treatment of urinary-tract infections. (Am. J. Health Syst. Pharm. 2001, 58 (12): p 1101-1109). For example the installation of *Lactobacillus*, and stimulation of indigenous organisms, has been employed to prevent recurrence of urinary tract infections (Microecol. Ther.: 32-45). The role of Lactobacilli in preventing urogenital and intestinal infections has also been investigated (Intl. Dairy J 1998.8: 555-562).

DESCRIPTION OF RELATED ART

The importance of Lactobacilli as probiotics has been described in the literature.

Jacobsen et al, Applied and Environmental Microbiology, (1999) 65, 4949-4956 discloses the screening of probiotic activities of forty-seven strains of *Lactobacillus* spp. by in vitro techniques and evaluation of the colonization ability of five selected strains in humans. The strains were examined for resistance to pH 2.5 and 0.3% oxgall, adhesion to Caco-2 cells and antimicrobial activities against enteric pathogenic bacteria. The average number of adhering Lactobacilli in 20 microscopic fields for example was 630±275 for *L. Rhamnosus* LGG and 713±188 for *L. Rhamnosus* 19070-2.

U.S. Pat. No. 5,032,399 discloses therapeutical beneficial strains of *L. acidophilus* and especially a strain characterized in that an average of at least 50 bacteria were found to adhere to one human small intestinal mucosal cell after a five minute incubation of the bacteria with the cell. The strain was also characterized with respect to lactic acid production and hardy growth.

WO 99/45099 discloses a novel strain of *L. plantarum* LB 931. This strain can be used for treating or preventing urogenital infections. The strain was able to adhere well to vaginal epithelial cells as well as to inhibit or prevent growth of different bacterial strains.

U.S. Pat. No. 5,645,830 relates to *Lactobacillus*, skim milk, *Lactobacillus* Growth Factor (LGF) and *Lactobacillus* compositions and methods of employing the compositions for preventing urogenital infections. More particularly, this invention relates to the ability of strains of hydrophobic or hydrophilic *Lactobacillus* to adhere to biomaterials, and intestinal, vaginal and uroepithelial cells, to resist the action of certain antimicrobial agents and to dominate the urogenital flora. In the case of *L. casei* var. *rhamnosus* GR-1, it was found that an average of at least 64 bacteria could adhere to one uroepithelial cell, whereas for *L. fermentum* B-54 an average of at least 39 bacteria could adhere to one uroepithelial cell.

U.S. Pat. No. 6,093,394 (WO 98/46261) discloses novel strains, e.g. *L. crispatus* CTV-05, isolated from vaginal smears. The strain is characterized by an increased ability to adhere to vaginal epithelial cells and to produce hydrogen peroxide. The *L. crispatus* CTV-05 was found to have a percent vaginal epithelial cell (VEC) cohesion value of greater than 50%. The "percent VEC cohesion value" is defined as the percentage of VECs to which at least one *Lactobacillus* cell has adhered in the total number of VECs in an identified group. The ability of these strains to colonize is ascribed to a novel preservation matrix disclosed in the document.

EP0956858 discloses the use of different *Lactobacillus* strains alone or in combination. The strains were selected based on their ability to adhere to HeLa cells and to produce hydrogen peroxide.

WO 97/29762 discloses compositions comprising an effective amount of at least one plant species of the Ericaceae family or its extract and a culture of at least one species of microencapsulated bacteria selected from the group consisting of *Lactobacillus, Bifidobacterium* and mixtures thereof. The composition is useful in preventing and/or treating urogenital and intestinal disorders.

In Ocaña et al, Biocell (2001) 25(3), 265-273 the capability of Lactobacilli to adhere to vaginal epithelial cells (VEC) was studied. The Lactobacilli, *L. crispatus* CRL 1266, *L. sali-*

*varius* subsp. *salivarius* CRL 1328, *L. acidophilus* CRL 1259, *L. acidophilus* CRL 1294 were isolated from human vaginal smears.

In McLean, N. W. et al, J. Med. Microbiol., 2000, 49 (6) pp 543-552 different Lactobacilli were characterized in order to assess their potential use as probiotics by investigating their capability to adhere to vaginal epithelial cells (VEC). The Lactobacilli were isolated from human vaginal smears.

Pharmaceutical compositions of Lactobacilli known in the art are not sufficiently efficient in recolonizing in vivo, i.e., in mammalian microbial ecosystems and there is therefore a need for finding Lactobacilli with an inherent ability to colonize upon administering the Lactobacilli in the form of a pharmaceutical composition, a nutraceutical, a dairy product, a functional food or absorbent product. Lactobacilli isolated from human sources will have the best ability to recolonize in vivo upon administration because of their inherent ability to survive in the human microbial ecosystem. It is often a cumbersome process to identify Lactobacilli strains with enhanced abilities to colonize upon administration and it is therefore important to select the best test systems to predict their in vivo ability to recolonize.

The capability of Lactobacilli to adhere to vaginal epithelial cells (VEC), cultured Caco-2 cells or other cell lines has been found to be an important factor and serve as a means to assess the ability of a probiotics strain to colonize and participate in the formation of a barrier to prevent colonization of pathogenic bacteria.

In the literature there seems to be a large variation in the reported in vitro adherence of probiotic strains. This variation indeed reflects biological differences between strains, but certainly also depends on experimental conditions. Moreover, there also seems to be variation with regard to how to measure the adherence. In U.S. Pat. No. 6,093,394 the adherence of Lactobacilli is determined by calculating the percent vaginal epithelial cell (VEC) cohesion value. The "percent VEC cohesion value" is defined as the percentage of VEC's, where at least one *Lactobacillus* cell is adhered in the total number of VECs in an identified group. Another measure of in vitro adherence is to count the average number of adhered microbial cells to a pre-defined number of epithelial cells in a stained preparation. According to the inventors the first method is better than the latter, inasmuch as it more closely reflects the in vivo adherence. It may be argued that an in vitro experiment only serves as a means to estimate the in vivo ability to colonize by adherence to epithelial cells of for example the vagina. The way the adherence is calculated is therefore not necessarily the most important factor, but rather it is very important to compare potential probiotic strains with a well-characterized probiotic bacterial strain that is known to adhere to a mucosal membrane. U.S. Pat. No. 5,032,399 discloses a Lactobacilli strain characterized in that an average of at least 50 of the bacteria can adhere to one human small intestinal mucosal cell, however the Lactobacilli strain is not compared to a well-characterized probiotic bacteria. *Lactobacillus casei* GG is an example of a commercially available, well-characterized probiotic strain that is relevant to use for comparison in the search for efficient probiotic strains.

Besides studying the adhesiveness of the Lactobacilli to exfoliated vaginal epithelial cells (VEC), cultured Caco-2 cells or other types of cell lines, it is also important to characterized the in vitro inhibitory activity of the Lactobacilli against bacterial species, e.g., anaerobic and mycoplasmal bacteria involved in bacterial vaginosis, acid production after growth of the Lactobacilli in liquid culture, and production of hydrogen peroxide ($H_2O_2$). It is important to measure the hydrogen peroxide production, because in vivo hydrogen peroxide will assist in eradicating non-hydrogen peroxide producing bacteria and mycoplasmal bacteria.

In summary, Lactobacilli strains with probiotic capabilities should be able to adhere to vaginal epithelial cells (VEC), and other suitable cells, such as the cell line Caco-2 cells. Moreover, it is also desirable that the Lactobacilli strains with probiotic capabilities show in vitro inhibitory activity against other bacterial species, produce acid after growth in liquid culture and/or produce hydrogen peroxide.

SUMMARY OF THE INVENTION

It is an object of the present invention to provide pharmaceutical formulations or absorbent products of suitable probiotic Lactobacilli strains with the desired properties as discussed above. More particularly the present invention concerns the *Lactobacillus gasseri* strain Lba EB01 (EB01), *Lactobacillus rhamnosus* strain Lbp PB01 (PB01), *Lactobacillus acidophilus* strain Lba EB02 (EB02), *Lactobacillus plantarum* strain Lbpl PB02 (PB02), *Lactobacillus* strain Lbxx EB03 (EB03) and *Lactobacillus* strain Lbxx PB03 (PB03), and strains with essentially the same advantageous properties e.g., the ability to colonize by adherence to mucosal membranes and which are therefore suited for the treatment or prevention of vaginal infections, urinary-tract infections and gastrointestinal diseases.

Another object of the present invention is to provide pharmaceutical formulations with an increased ability to colonize by adherence to the mucosal membrane by employing mucous adhesive excipients.

It is a further object of the present invention to provide vaginal formulations with an increased ability to suppress the growth of *Candida albicans* and Gram negative pathogenic bacteria.

It is yet another objective of the present invention to provide dairy products, nutraceutical products and functional food comprising one or more probiotic *Lactobacillus gasseri* strain Lba EB01, *Lactobacillus rhamnosus* strain Lbp PB01, *Lactobacillus acidophilus* strain Lba EB02, *Lactobacillus plantarum* strain Lbpl PB02, *Lactobacillus* strain Lbxx EB03, *Lactobacillus* strain Lbxx PB03 or strains with essentially the same properties having the ability to colonize mucosal membranes, and therefore adapted to the treatment or prevention of vaginal infections, urinary-tract infections and gastrointestinal diseases.

DEFINITIONS

By "excipient" is meant any non-active ingredient that is added to form part of the final formulation.

By "probiotic" is meant a viable microbial supplement, which has a beneficial influence on the patient through its effects in the intestinal tract, urinary tract or the vaginal tract.

A "prebiotic" is used herein as a substrate, which has a beneficial effect on a probiotic and thus on the individual patient taking the probiotic.

A "patient" is used herein as a person suffering from any clinical condition related to a microbial imbalance as well as a person using bacterial preparations prophylactically.

By a synbiotic product is meant a combination of probiotic and prebiotic, which in synergy, have a beneficial influence on the patient.

By "hardy growth" is meant that bacteria show excellent growth.

The abbreviation "cfu" means "colony-forming unit".

DETAILED DESCRIPTION OF THE INVENTION

The present invention relating to probiotic Lactobacilli strains capable of regenerating the in vivo flora in humans will become apparent in the progress of the following detailed description.

According to a first aspect, the present invention comprises *Lactobacillus gasseri* strain Lba EB01, *Lactobacillus rhamnosus* strain Lbp PB01, *Lactobacillus acidophilus* strain Lba EB02, *Lactobacillus plantarum* strain Lbpl PB02, *Lactobacillus* strain Lbxx EB03 and *Lactobacillus* strain Lbxx PB03 as well as probiotic *Lactobacillus* strains with essentially the same properties.

Particular examples of *Lactobacillus gasseri* strain Lba EB01 and *Lactobacillus rhamnosus* strain Lbp PB01 have been deposited at the DSMZ—Deutsche Sammlung Von Mikroorganismen und Zellkulturen Gmbh, MascheroderWeg 1b, D-38124 Braunschweig, Germany and given the following accession numbers: *Lactobacillus gasseri* Lba EB01; DSM 14869 and *Lactobacillus rhamnosus* Lbp PB01; DSM. 14870. The date of the deposit of *Lactobacillus gasseri* strain EB01 and *Lactobacillus rhamnosus* strain PB01 was 18 Mar. 2002.

Particular examples of *Lactobacillus acidophilus* strain Lba EB02, *Lactobacillus plantarum* strain Lbpl PB02, *Lactobacillus* strain Lbxx EB03 and *Lactobacillus* strain Lbxx P803 have been deposited at the DSMZ—Deutsche Sammlung Von Mikroorganismen und Zellkulturen Gmbh, Mascheroder Weg 1b, D-38124, Germany. The date of the deposit of *Lactobacillus acidophilus* strain Lba EB02, *Lactobacillus plantarum* strain Lbpl PB02, *Lactobacillus* strain Lbxx EB03 and *Lactobacillus* strain Lbxx P803 was 20 Mar. 2003. The strains were given the following accession numbers:

*Lactobacillus acidophilus* strain Lba EB02, . . . .
*Lactobacillus plantarum* strain Lbpl PB02, . . . .
*Lactobacillus* strain Lbxx EB03 . . . .
*Lactobacillus* strain Lbxx PB03 . . . .

The Lactobacilli strains have the following properties;

*Lactobacillus gasseri* Strain Lba EB01
At least 20% of added bacteria adhere to cultured Caco-2 cells during a one-hour incubation period.
The adherence to vaginal epithelial cells (VEC) is at least 15 bacteria per cell.
The strain produces hydrogen peroxide.
The strain produces lactic acid in vitro and shows hardy growth in vitro.
The strain shows bile stability.
The strain shows acid stability.
The strain produces a natural antibiotic substance in the form of a bacteriocin.

*Lactobacillus rhamnosus* strain Lbp PB01
At least 30% of added bacteria adhered to cultured Caco-2 cells during a one-hour incubation period.
The adherence to vaginal epithelial cells (VEC) is 20 bacteria per cell.
The strain produces lactic acid in vitro and hardy growth in vitro.
The strain shows bile stability.
The strain shows acid stability.
The strain produces a natural antibiotic substance in the form of bacteriocins.
The strain demonstrates strong inhibitory activity against *Gardnerella*.

*Lactobacillus acidophilus* Strain Lba EB02
The bacteria adhere to cultured Caco-2 cells during a one-hour incubation period.
The bacteria adhere to vaginal epithelial cells (VEC).
The strain produces hydrogen peroxide.
The strain produces lactic acid in vitro and shows hardy growth in vitro.
The strain shows bile stability.
The strain shows acid stability.
The strain produces a natural antibiotic substance in the form of bacteriocins.

*Lactobacillus plantarum* Strain Lbpl PB02
The bacteria adhere to cultured Caco-2 cells during a one-hour incubation period.
The bacteria adhere to vaginal epithelial cells (VEC).
The strain produces hydrogen peroxide.
The strain produces lactic acid in vitro and shows hardy growth in vitro.
The strain shows bile stability.
The strain shows acid stability.
The strain produces a natural antibiotic substance in the form of a bacteriocin.

*Lactobacillus* Strain Lbxx EB03
At least 12% of added bacteria adhere to cultured Caco-2 cells during a one-hour incubation period.
The bacteria adhere to vaginal epithelial cells (VEC).
The strain produces lactic acid in vitro and shows hardy growth in vitro.
The strain shows bile stability.
The strain shows acid stability.
The strain produces a natural antibiotic substance in the form of bacteriocins.

*Lactobacillus* strain Lbxx PB03
At least 11% of added bacteria adhere to cultured Caco-2 cells during a one-hour incubation period.
The bacteria adhere to vaginal epithelial cells (VEC).
The strain produces lactic acid in vitro and shows hardy growth in vitro.
The strain shows bile stability.
The strain shows acid stability.
The strain produces a natural antibiotic substance in the form of bacteriocins.

By "probiotic *Lactobacillus* strain with essentially the same properties" is meant any strain, which has the same adherence properties as listed above for *Lactobacillus gasseri* strain Lba EB01, *Lactobacillus rhamnosus* Lbp strain PB01, *Lactobacillus acidophilus* strain Lba EB02, *Lactobacillus plantarum* strain Lbpl PB02, *Lactobacillus* strain Lbxx EB03 and *Lactobacillus* strain Lbxx PB03, preferably for *Lactobacillus gasseri* strain Lba EB01, *Lactobacillus rhamnosus* Lbp strain PB01, *Lactobacillus* strain Lbxx EB03 and *Lactobacillus* strain Lbxx PB03 and more preferably *Lactobacillus gasseri* strain Lba EB01 and *Lactobacillus rhamnosus* Lbp strain PB01.

In order to determine the genus and species of the strains disclosed herein the Riboprinter© Microbial Characterization system was employed. The amount and composition of the strains were identified and determined by gas chromatography. Moreover, an API identification of the strains was also carried out.

The adherence properties of the isolated strains were compared to the well-characterised probiotic strain *Lactobacillus casei* GG. Almost 30% of the added *Lactobacillus rhamnosus* PB01 strain bacteria adhered to the cultured Caco-2 cells during a one-hour incubation period, compared to about 20% of the *Lactobacillus gasseri* strain EB01 and about 10% of *Lactobacillus* GG. *Lactobacillus rhamnosus* strain PB01 adheres most strongly to the VEC with approximately 20 bacteria per cell after a one-hour incubation. *Lactobacillus* GG has the lowest number of adhered bacteria, while strain EB01 has intermediate values. The adhesion of these three bacterial strains to the cultured Caco-2 correlated well to the adhesion to the VEC.

*Lactobacillus acidophilus* strain Lba EB02 and *Lactobacillus plantarum* strain Lbpl PB02 were found to adhere to cultured Caco-2 cells during a one-hour incubation period. At least 12% of added *Lactobacillus* strain Lbxx EB03 adhere to cultured Caco-2 cells during a one-hour incubation period, whereas at least 11% of added *Lactobacillus* strain Lbxx EB03 adheres to cultured Caco-2 cells during a one-hour incubation period.

Thus, all the strains were able to adhere to Caco-2 cells. Strain EB03 and PB03 had better adherence properties than *Lactobacillus casei* GG.

The strains were found to produce lactic acid in vitro and show hardy growth in vitro as well as show stability toward acid and bile, moreover both strains were able to produce natural antibiotic substance, bacteriocin Strain EB02 and PB02 showed a very strong ability to produce $H_2O_2$ and lactic acid *Lactobacillus rhamnosus*, strain PB01 has demonstrated a strong inhibitory activity against the BV-associated bacterial species *Gardnerella vaginalis*. Strain EB01 produces $H_2O_2$. A combination of these two strains is very suitable for a vaginal probiotic product due to their supplementary effects. This is further supported by the finding that both isolates produced a highly acidic environment after growth in liquid medium and both strongly adhere to VEC and to cultured Caco-2 cells. The result also indicates that *Lactobacillus rhamnosus*, strain Lbp PB01 or Strain EB01 alone, in combination or together with *Lactobacillus acidophilus* strain Lba EB02, *Lactobacillus plantarum* strain Lbpl PB02, *Lactobacillus* strain Lbxx EB03 and *Lactobacillus* strain Lbxx PB03 are suitable for other administration routes.

According to a second aspect, the *Lactobacillus* strains of the present invention are suitable for medical use in preventing or treating vaginal infections, urogenital infections or gastrointestinal infections.

In a preferred embodiment, the curative effect of the probiotic *Lactobacillus* strains for treating vaginal infections is assessed by determining the vaginal flora by employing the Riboprinter© Microbial Characterization system. The Riboprinter© Microbial Characterization system is employed for determining the genus and species of microorganism. The patient is assessed as being cured when the vaginal flora is determined as being normal using the Riboprinter© Microbial Characterization system.

In another preferred embodiment, a pharmaceutical composition is provided comprising one or more probiotic *Lactobacillus* strains used according to the invention together with a pharmaceutically acceptable carrier and/or diluent. The bacterial strains are formulated into pharmaceutical formulations in order to allow the easy administration of the probiotic strains and by means known to the man skilled in the art.

Preferably, the probiotic bacteria employed in a pharmaceutical composition in accordance with the present invention are used in bacterial concentrations of $10^5$ to $10^{13}$ cfu *Lactobacillus* per gram, more preferably $10^6$ to $10^{12}$ cfu *Lactobacillus* per gram, where the abbreviation "cfu" means "colony-forming unit". This may be one of the strains or a combination thereof.

Preferably, the probiotic bacteria employed in accordance with the present invention is used directly, or more preferably in a lyophilized form.

For practical use the pharmaceutical compositions of the invention are prepared in the form of a suspension, spray, gel, cream, powder, capsule, solution for lavages, ovules, a vaginal insert, tablets or a microencapsulated product employing excipients and formulation techniques known to those skilled in the art.

In order to increase the ability of a pharmaceutical formulation to adhere to a mucosal membrane, mucous adhesive excipients may be added to comprise up to about 10% of the pharmaceutical formulation. The preferred mucous adhesive excipient is a hydrocolloid, more preferably the hydrocolloid is selected from the group comprising xanthan gum, locust bean gum alginate and most preferably the hydrocolloid is xanthan gum.

*Candida albicans* are not able to ferment lactitol and this may also be the case for *E. coli* or other Gram negative bacteria. Therefore, a prebiotic substrate which is not fermented by *Candida albicans* or by pathogenic bacteria is employed in vaginal formulations comprising the probiotic Lactobacilli strains used according to the present invent in order to suppress the growth of *Candida albicans*. The prebiotic substrate is preferably an oligosaccharide, more preferably the substrate is lactitol, oligofructose or lactulose, most preferably the substrate is lactitol.

In another preferred embodiment of the present invention, an absorbent product is provided comprising one or more probiotic Lactobacilli strains. The bacterial strains are incorporated into absorbent products in order to allow the convenient administration of the probiotic strains during use of the absorbent product.

For practical use the absorbent product of the present invention is a feminine hygiene diaper, sanitary napkin, impregnated tampon, panty guard or an incontinence guard comprising one or more *Lactobacillus* strains. Preferably, the probiotic bacteria employed in the absorbent product are used in bacterial concentrations of $10^5$ to $10^{13}$ cfu *Lactobacillus*, more preferably $10^6$ to $10^{12}$ cfu *Lactobacillus*.

In a preferred embodiment of the present invention, dairy products are provided comprising one or more probiotic *Lactobacillus* strains, the bacterial strains are incorporated into dairy products which allow oral administration of the probiotic strains for treating of preventing gastrointestinal diseases. Non-limiting examples of a dairy product is mild yoghurt, which is especially suitable together with the new probiotic strains (fermented milk), curdled milk and whole milk.

In another preferred embodiment of the present invention, nutraceutical products are provided comprising one or more probiotic *Lactobacillus* strains, the bacterial strains are incorporated into nutraceutical products for allowing oral administration of the probiotic strains for treating or preventing gastrointestinal diseases. Non-limiting examples of nutraceutical products are products used to supplement the diet and with a positive effect on the health.

In yet another preferred embodiment of the present invention, functional food is provided comprising one or more probiotic *Lactobacillus* strains, the bacterial strains are incorporated into functional food allowing oral administration of the probiotic strains for treating of preventing gastrointestinal diseases. Non-limiting examples of functional food products are freeze dried and microencapsulated products for easy spread on food products.

In a further preferred embodiment of the present invention, the *Lactobacillus* strains are used for preparing pharmaceutical compositions for preventing and/or treating vaginal infections, gastrointestinal diseases or urinary-tract infections.

In yet a further preferred embodiment of the present invention, the *Lactobacillus* strains are used for producing an absorbent product, such as a feminine hygiene diaper, sanitary napkin, panty guard or an incontinence guard for preventing and/or treating vaginal infections, gastrointestinal diseases or urinary-tract infections.

In another preferred embodiment of the present invention, the *Lactobacillus* strains are used for preparing dairy products for preventing and/or treating gastrointestinal diseases.

In yet another preferred embodiment of the present invention, the *Lactobacillus* strains are used for preparing functional foods for preventing and/or treating gastrointestinal diseases.

In a further preferred embodiment of the present invention the *Lactobacillus* strains are used for preparing nutraceuticals for preventing gastrointestinal diseases.

The treatment schedule of these different products will depend on the product in question and the patient, which are known to those skilled in the art. A non-limiting example of a treatment schedule for vaginal capsules is one vaginal capsule twice a day for seven days.

In order to give the bacteria optimum growth conditions initially and thus enabling the bacteria to recolonize by adherence in vivo, it is important to incorporate a substrate, i.e., a specific nutritional growth medium for the bacteria, into the formulation. The substrate will serve as a functional prebiotic, which together with the probiotic has a synergistically beneficial effect on the patient, i.e., the prebiotic and the probiotic acts as a symbiotic. Lactose is an example of such a substrate; however lactose also serves as a substrate for the pathogen *Candida albicans* and Gram negative pathogenic bacteria. It may therefore be relevant to provide a bacterial formulation with a substrate, which is not a substrate for *Candida albicans*. In a third aspect of the invention, there is therefore provided vaginal formulations comprising bacterial strains with the ability to colonize the vagina and a substrate, which is not fermented by *Candida albicans*. Preferably the substrate is an oligosaccharide, more preferably the substrate is lactitol, oligofructose and/or lactulose, most preferably the substrate is lactitol.

The effect of lactitol on the in vitro adherence of *Lactobacillus gasseri* strain Lba EB01 and *Lactobacillus rhamnosus* strain Lbp PB01 to the HEp-2 cell line and the WEHI cell line was studied. It was found that the lactitol does not affect the overall ability of the bacterial strains to adhere to the cells and will thus neither affect the in vivo adherence.

In a preferred embodiment of the present invention a substrate, which is not or not easily fermented by *Candida albicans* or by Gram negative pathogenic bacteria is used in the preparation of a vaginal formulation comprising bacteria in order to suppress the growth of *Candida albicans*, the substrate is preferably an oligosaccharid, more preferably the substrate is lactitol, oligofructose and/or lactulose and most preferably the substrate is lactitol.

In yet a preferred embodiment of the present invention, the bacterial strains in the form of, e.g., capsules are use as medical devices in order to obtain a stable mammalian microbial ecosystem in vivo.

EXAMPLES

Example 1

Isolation of Bacterial Strains

Two *Lactobacillus* strains, typed as *Lactobacillus gasseri* Lba EB01 and *Lactobacillus rhamnosus* Lbp PB01, were isolated from vaginal epithelial cells obtained from healthy human donors, and have been deposited at DSMZ. *Lactobacillus gasseri* Lba EB01 was given the following accession number; DSM 14869 and *Lactobacillus* rhamnosus Lbp PB01 was given the following accession number; DSM 14870. The date of deposit was 18 Mar. 2002.

Four *Lactobacillus* strains, typed as *Lactobacillus acidophilus* strain Lba EB02, *Lactobacillus plantarum* strain Lbpl PB02, *Lactobacillus* strain Lbxx EB03 and *Lactobacillus* strain Lbxx PB03, were isolated from vaginal epithelial cells obtained from healthy human donors, and have been deposited at DSMZ. The date of deposit was 20 Mar. 2003.

*Lactobacillus casei* GG, a commercially available probiotic, was obtained from Valio (Finland). These strains were cultured anaerobically in Man, Rogosa and Sharpe broth (Merck) at 37° C.

For radio labeling, 40 µl $^3$H-adenine was added to 20 ml broth and incubated for 16-18 hours, and excess radiolabel was removed by washing and centrifugation of the bacteria the twice. Bacteria used in the VEC-assay were not radiolabelled, but otherwise handled as described above. Optical density at 600 nm of bacterial cultures was used to adjust bacterial concentrations as indicated elsewhere.

Example 2

Adherence of Probiotic Strains to VEC

By this test the adherence of probiotic Lactobacilli strains to VEC was investigated.

VEC were harvested, during gynecological investigation, into sterile phosphate buffer saline (PBS) pH 7.2. After about 20 hours, gentamicin and fetal bovine serum were added to the cells. Final concentrations were 100 µg/ml gentamicin and 2% serum. The cells were then stored for another 24 hours at 4° C. Prior to the adherence assay, the cells were washed twice using PBS-buffer with 2% serum.

The washed probiotic strains were suspended in 10 mM lactate and 150 mM NaCl pH 4.5 buffer and the optical density was adjusted to 1.00±0.03. The bacterial suspension was mixed 1:1 with VEC-suspension and incubated for 2 hours at 37° C. After incubation the cells were washed 4 times using PBS-buffer with 2% fetal bovine serum and finally washed once using plain PBS. After the last centrifugation, the cell pellet was suspended in a few microliters of the buffer and transferred to microscope slides. The cells were then dried at 90° C. The dried spot was fixed with methanol and stained with 0.1% crystal violet. The stained preparation was studied using a light microscope with oil immersion at 100×. The number of bacteria was counted on 30-70 randomly chosen cells/donor.

Figure 2:
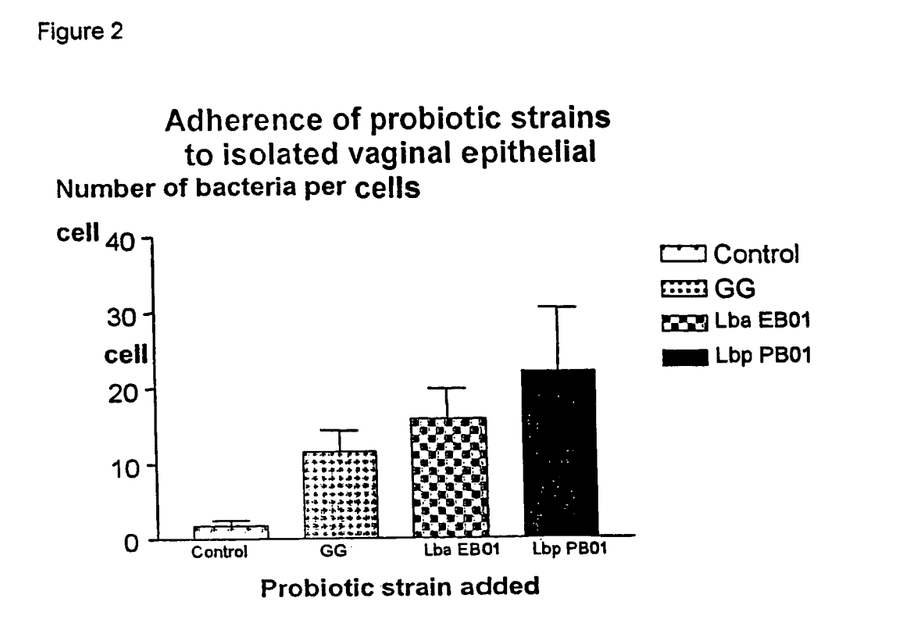
FIG. 2 Adherence of *Lactobacillus gasseri* strain EB01, *Lactobacillus* rhamnosus strain PB01 and *Lactobacillus casei* GG to isolated vaginal epithelial cells. The number of bound bacteria was calculated and is presented as the number of bound bacteria per VEC cells±SD.

The results presented in FIG. 2 shows the adherence of the three strains to VEC. The values are the mean±SD from 5 donors. Strain PB01 adheres most strongly with approximately 20 bacteria per cell after one-hour incubation. *Lactobacillus* GG has the lowest number of adhered bacteria, while strain EB01 has intermediate values.

Example 3

Adherence of Probiotic Strains to Caco-2 Cell Cultures

By this test the adherence of probiotic Lactobacilli strains to Caco-2 cells was investigated.

The Caco-2 cell line (CRL-2102, ATCC, USA) was cultured in Dulbecco's modified Eagle's medium (Sigma-Aldrich) with 4 mM L-glutamine adjusted to contain 4.5 g/L glucose, 1.5 g/L sodium bicarbonate, 1.0 mM sodium pyruvate (Sigma-Aldrich), 10% fetal calf serum (FBS) (Merck) and 1% penicillin/streptomycin (Merck) at 37° C. in an atmosphere of 5% $CO_2$/95% air. For adherence assays, Caco-2 cells were seeded at a concentration of $1.5 \times 10^5$ in 96-well microtiter plates. The cell cultures were maintained for 2 weeks prior to use. The cell culture medium was changed every other day, and it was changed 2 hours before the adherence assay.

The adherence of bacterial strains to Caco-2 cell cultures was examined by adding 200 µl of radio labelled bacterial suspension to the wells. Before adding the bacteria, the wells were washed twice with MEM-Eagle (Sigma-Aldrich) supplemented with 0.5% FBS, 1% L-glutamine and 0.1% non-essential amino acids. After incubation for one hour, the cell cultures were washed 4 times with 250 µl buffered saline solution in a Multiwash Plus AR (Labsystems) and treated with 150 µl of 2% SDS in 0.01 M NaOH for 20 minutes to lyse the bacteria, which were measured by liquid scintillation counting. The adherence ratio (%) was calculated by comparing the radioactivity with the original bacterial suspension.

Figure 1:
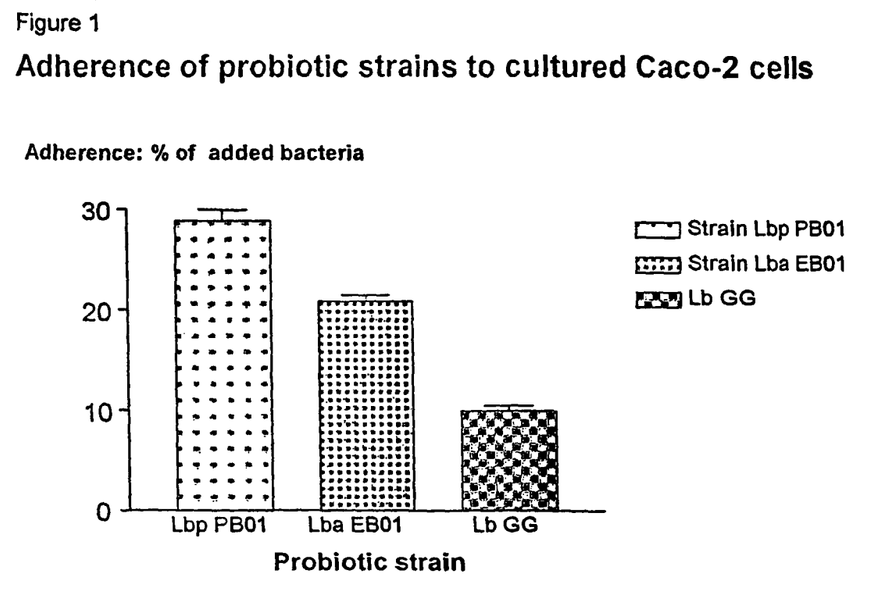
FIG. 1 Adherence of *Lactobacillus gasseri* strain EB01, *Lactobacillus* rhamnosus strain PB01 and *Lactobacillus casei* GG to cultured Caco-2 cells. The number of bound bacteria was calculated and is presented as mean percent adherence±SD.

The data presented in FIG. 1 shows the adherence of the three probiotic strains to cultured Caco-2 cells.

Almost 30% of the added *Lactobacillus rhamnosus* Lbp PB01 strain bacteria adhered to the cultured cells during the one-hour incubation period, in comparison to about 20% of the *Lactobacillus gasseri* strain Lba EB01 and about 10% of *Lacobacillus* GG.

Example 4

Correlation of Adherence to Cultered Caco-2 Cells Compared to VEC

Figure 3:
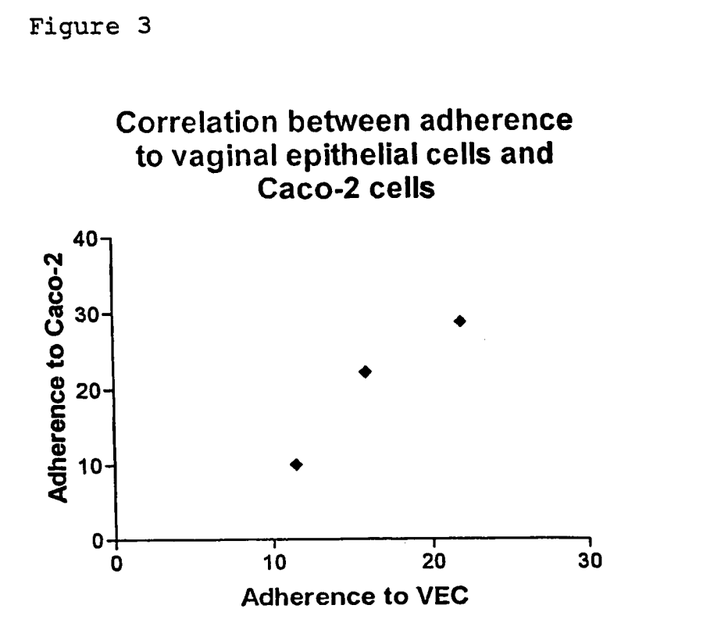
FIG. 3 Correlation between adherence to VEC and Caco-2 cells. The figure is based on data in FIG. 1 and FIG. 2

As shown in FIG. 3 there is a good correlation between adherence to cultured Caco-2 cells and to VEC.

Example 5

Composition for Vaginal Capsules

| Ingredients: | mg/capsule: |
|---|---|
| Lactitol | 328.00 |
| Glucose | 20.00 |

-continued

| Ingredients: | mg/capsule: |
|---|---|
| Xanthan gum | 25.00 |
| *Lactobacillus acidophillus* Lba EB01 | 12.50 |
| *Lactobacillus paracasei* Lbp PB01 | 12.50 |
| Magnesium stearate | 2.00 |

The freeze-dried lactic acid culture was kept free from foreign contamination until use. A nutritive growth medium consisting of anhydrous glucose, anhydrous lactitol and xanthan gum was found to be optimal for the lactic bacteria. Magnesium stearate is a hydrophobic anti-adhesion lubricant to ensure powder flow during filling into capsules.

All the excipients were sieved employing a Frewitt sieve, and mixed employing a Cubus mixer. The homogenous powder was then filled into capsules.

All processes are performed according to general pharmaceutical practice.

The raw material culture, the excipients and the finished product are controlled thoroughly by using validated analytical methods for identification, purity, contamination and assay.

Example 6

Composition for Chewable Tablets

| Ingredients: | mg/tablet: |
|---|---|
| Lactitol | 330.50 |
| Xylitol | 90.00 |
| Mandarin aroma | 3.50 |
| Lactic acid | 9.00 |
| Dual coated *Lactobacillus* Lbp *paracasei* | 6.25 |
| Dual coated *Lactobacillus* Lba *Acidophillus* | 6.25 |
| Magnesium stearate | 4.50 |

The freeze-dried lactic acid culture is kept free from foreign contamination until use. The nutritive growth medium, lactitol, was found to be optimal for the lactic bacteria.

Magnesium stearate is a hydrophobic anti-adhesion lubricant to ensure powder flow during tablet compression. Mandarin aroma powder and lactic acid powder is added for flavour.

All the excipients were sieved employing a Frewitt sieve and mixed employing a Cubus mixer. The homogenous powder was then made into tablets with a tablet weight of 450 mg.

All processes are performed according to general pharmaceutical practice.

The raw material culture, the excipients and the finished product are controlled thoroughly by using validated analytical methods for identification, purity, contamination and assay.

Example 7

Composition for a Dairy Product

Preparation of Probiotic *Lactobacillus gasseri* Strain Lba EB01 and Yoghurt Cultures The skimmed milk is pasteurised at extra high temperatures, approximately 98° C. for at least 3 minutes. Powdered skimmed milk or powdered whey can be supplied during this process in order to raise the dry matter percentage.

The high-pasteurised skimmed milk is then fat and protein standardized to final percentage of fat of 3.5-4.0%, and of protein of 3.8-4.0%.

The standardized milk is then homogenized at a temperature of 60-70° C. and at a pressure of 200-220 bar (20-22 Mpa).

The standardized and homogenized milk is then pasteurized at 90-98° C. for 3-5 minutes.

The milk is then cooled and pumped into a fermenter for incubation at a constant fermenting temperature at 35-40° C. throughout the fermenting process.

Yoghurt sole starter culture, as well as the sole starter Probiotic Lactobacilli strain Lba EB01 are poured directly into the milk while stirring powerfully. The fermenting cultures 'the sole starters' are supplied from e.g. frozen cultures (pellets stored at −40° C. before use) and directly filled into the fermenter.

The fermenting process is ongoing until the pH level is: 4.6-4.4.

Then the yoghurt is stirred and cooled to 20-25° C.

The yoghurt is then cooled down to approximately 20-24° C. and pumped directly into a buffer tank, where it is kept at 20° C. until filling into the final packaging material (with or without fruit jam), and stored cold at 2-5° C.

Example 8

Vaginal Capsules Pilot Study

Clinical test: Effect and level of patient satisfaction.

The goals of the pilot study were (1.) to examine the clinical effect of Vaginal capsules in women diagnosed with Bacterial Vaginosis (BV) and (2.) to examine whether the vaginal capsules are patient-oriented.

The group of patients was 21 women diagnosed with BV. The doctor diagnosed BV according to the following criteria:
- Women with a malodorous vaginal discharge
- Excess grey and whitish discharge
- pH higher than 4.5
- Positive odor test Dosage Form:
Vaginal capsules prepared according example 5 contains human lactic acid bacteria (Lba EB01 and Lbp PB01).

Treatment:
After having been diagnosed, the women were treated one week with Vaginal capsules.

Two to three weeks after the treatment the women were clinically by examined and then asked to fill out a "patient" questionnaire.

Study Place:
The study was carried out at the gynecological clinic in Drammen (Norway).

Result:
All patients suffered from malodorous vaginal discharge. In addition, 12 suffered from excess discharge, 5 suffered from minor bleeding while 3 mentioned discomfort from itchiness.

Two-thirds of the patients had suffered for several years. Thirteen (62%) had tried self-medication: 8 with Canesten against fungus, 3 with lactic acid suppositories, and 1 with antibiotic treatment. Twelve of the patients had consulted their doctor, and 50% were given fungicide, 25% Dalacin against BV, while 25% did not receive any treatment at all.

Ninety percent of the women (19 out of 21) found that the symptoms disappeared during the treatment and most of them within a few days:

within 2 days: 6 women within 5 days: 9 women within 8 days: 4 women

One woman found the vaginal capsules hard to apply while the remaining 20 women were very pleased. All women with the exception of one (1 of the 2 who did not find the treatment effective) wanted to try vaginal capsules again in case of recurrence. No side effects were reported.

Conclusion:

Vaginal capsules containing bacterial strains according to the invention seem to have a positive clinical effect on women suffering from the symptoms connected with BV and 9 out of 10 were cured.

Most of the patients had tried self-medication and consulted their doctor. Most of them had tried fungicides to relieve the discomfort.

The vaginal capsules were considered very user-friendly.

Example 9

In order to test the in vivo effect in women of lactitol in a prebiotic formulation according to the invention, different vaginal formulations were manufactured.

Composition for Vaginal Capsules (with Lactitol)

| Ingredients: | mg/capsule: |
| --- | --- |
| Lactitol | 328.0 |
| Glucose | 20.0 |
| Xanthan gum | 25.0 |
| *Lactobacillus acidophillus* Lba EB01 | 12.5 |
| *Lactobacillus paracasei* Lbp PB01 | 12.5 |
| Magnesium stearate | 2.0 |

Composition for Vaginal Capsules (with Lactose)

| Ingredients: | mg/capsule: |
| --- | --- |
| Lactose | 328.0 |
| Glucose | 20.0 |
| Xanthan gum | 25.0 |
| *Lactobacillus acidophillus* Lba EB01 | 12.5 |
| *Lactobacillus paracasei* Lbp PB01 | 12.5 |
| Magnesium stearate | 2.0 |

Composition for Vaginal Capsules (without Bacterial Strains)

| Ingredients: | mg/capsule: |
| --- | --- |
| Lactitol | 353.0 |
| Glucose | 20.0 |
| Xanthan gum | 25.0 |
| Magnesium stearate | 2.0 |

Vaginal capsules containing bacterial strains and lactitol are preferred dosage forms for treating women with gynecological problems.

Example 10

| Riboprint of *Lactobacillus gasseri* Lba EB01 (=1702 BBB *Lactobacillus acidophilus*) and *Lactobacillus rhamnosus* Lbp PB01 (=1704 BBB *Lactobacillus Paracesei*). | |
|---|---|
| Label/Presumptive ID | RiboPrint(R) Pattern |
| *Lactobacillus paracasei* ss. *paracasei* <Unlabeled> <none> | |
| *Lactobacillus paracasei* ss. *paracasei* <Unlabeled> <none> | |
| 1704 BBB *Lactobacillus paracasei* | |
| *Lactobacillus rhamnosus* <Unlabeled> <none> | |
| *Lactobacillus rhamnosus* <Unlabeled> <none> | |
| *Lactobacillus acidophilus* <Unlabeled> <none> | |
| *Lactobacillus acidophilus* <Unlabeled> <none> | |
| 1702 BBB *Lactobacillus acidaphilus* | |
| *Lactobacillus gasseri* <Unlabeled> <none> | |
| *Lactobacillus johnsonii* <Unlabeled> <none> | |

Example 11

The fatty acid composition of *Lactobacillus gasseri* Lba EB01 and *Lactobacillus rhamnosus* Lbp PB01.

| Reference database *Lb. Acidophilus* | | Reference database *Lb. Paracasei* | | Test *Lb. Acidophilus* Lba EB01 | | Test *Lb. Paracasei* Lbp PB01 | |
|---|---|---|---|---|---|---|---|
| Fatty acid | Percent | Fatty acid | Percent | Fatty acid | Percent | Fatty acid | Percent |
| 14:0 | 4.09 | 14:0 | 5.25 | 14:0 | 9.79 | 14:0 | 6.22 |
| 16:0 | 7.91 | 16:0 | 16.17 | 16:0 | 34.64 | 16:0 | 37.32 |
| 17:1 w8c | 1.24 | 17:1 w8c | 0.6 | 17:1 w8c | 0 | 17:1 w8c | 0 |
| 18:1 w9c | 63.03 | 18:1 w9c | 44.07 | 18:1 w9c | 32.79 | 18:1 w9c | 37.45 |
| 18:1 w7c | 6.17 | 18:1 w7c | 13.18 | 18:1 w7c | 0 | 18:1 w7c | 5.56 |
| 18:0 | 0.9 | 18:0 | 1.05 | 18:0 | 8.17 | 18:0 | 7.04 |
| sum in feature 3 | 5.71 | sum in feature 3 | 9.47 | sum in feature 3 | 0 | sum in feature 3 | 0 |
| sum in feature 5 | 2.16 | sum in feature 5 | 0.56 | sum in feature 5 | 14.6 | sum in feature 5 | 6.41 |
| sum in feature 7 | 7.09 | sum in feature 7 | 8.3 | sum in feature 7 | 0 | sum in feature 7 | 0 |
| total % | 98.3 | | 98.65 | | 99.99 | | 100 |

Example 12

The API of *Lactobacillus acidophilus* Lba EB01 and *Lactobacillus paracasei* Lbp PB01 showing the ability of the strains to ferment different sugars.[1]

[1] *Lactobacillus acidophilus* Lba EB01 (DSM 14869) was later classified as *Lactobacillus gasseri*. *Lactobacillus paracasei* Lbp PB01 (DSM 14870) was later classified as *Lactobacillus rhamnosus*.

Number 1=*Lactobacillus acidophilus* Lba EB01 (DSM 14869)

Number 2=*Lactobacillus paracasei* Lbp PB01 (DSM 14870)

Overall Conclusion: Number 1=*Lactobacillus acidophilus*

The API 50 CHL result gave a very good result with regard to the genus, which was found to be correct (*Lactobacillus* spp), whereas the identification with regard to the species (*L. acidophilus*) is not as certain.

Results:

| API50CHL | 1. .:- |
|---|---|
| Glycerol | Negativ |
| Erythritol | Negativ |
| D-Arabinose | Negativ |
| L-Arabinose | Negativ |
| Ribose | Negativ |
| D-Xylose | Negativ |
| L-Xylose | Negativ |
| Adonitol | Negativ |
| β Methyl-D-xylosid | Negativ |
| Galactose | Positiv |
| Glucose | Positiv |
| Fructose | Positiv |
| Mannose | Negativ |
| Sorbose | Negativ |

| API50CHL | 1. |
|---|---|
| Rhamnose | Negativ |
| Duicitol | Negativ |
| Inositol | Negativ |
| Mannitol | Negativ |
| Sorbitol | Negativ |
| α Methyl-D-mannosid | Negativ |
| α Methyl-D-glucosid | Negativ |
| N Acetyl glucosamin | Negativ |
| Amygdalin | Negativ |

-continued

| Arbutin | Negativ |
|---|---|
| Esculin | Positiv |
| Salicin | Negativ |
| Cellobiose | Positiv |
| Maltose | Positiv |
| Lactose | Negativ |
| Melibiose | Negativ |
| Sucrose | Positiv |
| Trehalose | Negativ |
| Inulin | Negativ |
| Melezitose | Negativ |
| D-Raffinose | Negativ |
| Stivelse | Negativ |
| Glycogen | Negativ |

-continued

| | | |
|---|---|---|
| Xylitol | Negativ | |
| Gentiobiose | Positiv | |
| D-Turanose | Negativ | |
| D-Lyxose | Negativ | |
| D-Tagatose | Negativ | |
| D-Fucose | Negativ | |
| L-Fucose | Negativ | |
| D-Arabitol | Negativ | |
| L-Arabitol | Negativ | |
| Gluconat | Negativ | |
| 2-Keto-gluconat | Negativ | |
| 5-Keto-gluconat | Negativ | |

| Conclusion | ID % | T-value (Complete identity to type strain = 1.00) |
|---|---|---|
| Lacto.acidophllus | 60.7 | 0.74 |
| Lacto.delb.delb. | 36.5 | 0.69 |
| Lacto.acidophllus | 2.5 | 0.59 |

Overall Conclusion: Number 2=*Lactobacillus Paracasei*

The API 50 CHL result gave a very good result with regard to the genus as well as species, thus is asserted that the strain is a *Lactobacillus Paracasei* subsp. *Paracasei*.

| API5OCHL | 2.~ |
|---|---|
| Glycerol | Negativ |
| Erythritol | Negativ |
| D-Arabinose | Negativ |
| L-Arabinose | Negativ |
| Ribose | Positiv |
| D-Xylose | Negativ |
| L-Xylose | Negativ |
| Adonitol | Negativ |
| β Methyl-D-xylosid | Negativ |
| Galactose | Positiv |
| Glucose | Positiv |
| Fructose | Positiv |
| Mannose | Positiv |
| Sorbose | Positiv |
| Rhamnose | Negativ |
| Duicitol | Positiv |
| Inositol | Negativ |
| Mannitol | Positiv |
| Sorbitol | Positiv |
| α Methyl-D-mannosid | Negativ |
| α Methyl-D-glucosid | Positiv |
| N Acetyl glucosamin | Positiv |
| Amygdalin | Positiv |
| Arbutin | Positiv |
| Esculin | Positiv |
| Salicin | Positiv |
| Cellobiose | Positiv |
| Maltose | Negativ |
| Lactose | Positiv |
| Melibiose | Negativ |
| Sucrose | Negativ |
| Trehalose | Positiv |
| Inulin | Negativ |
| Melezitose | Positiv |

-continued

| API5OCHL | 2.~ |
|---|---|
| D-Raffinose | Negativ |
| Stivelse | Negativ |
| Glycogen | Negativ |
| Xylitol | Negativ |
| Gentiobiose | Negativ |
| D-Turanose | Negativ |
| D-Lyxose | Negativ |
| D-Tagatose | Positiv |
| D-Fucose | Negativ |
| L-Fucose | Negativ |
| D-Arabitol | Negativ |
| L-Arabitol | Negativ |
| Gluconat | Positiv |
| 2-Keto-gluconat | Negativ |
| 5-Keto-gluconat | Negativ |
| Conclusion | (Complete identity to type strain (complete = 1.00): 0.52 |
| *Lacto.para.paracasei* | ID % = 97.8 |

The invention claimed is:

1. An isolated probiotic *Lactobacillus* strain consisting of *Lactobacillus rhamnosus* strain Lbp PB01 (DSM 14870).

2. The isolated *Lactobacillus rhamnosus* strain Lbp PB01 (DSM 14870) according to claim 1 for medical use.

3. A pharmaceutical composition comprising the *Lactobacillus rhamnosus* strain Lbp PB01 (DSM 14870) according to claim 1 together with a pharmaceutically acceptable carrier and/or a diluent.

4. The pharmaceutical composition according to claim 3 comprising $10^5$ to $10^{13}$ cfu *Lactobacillus* per gram.

5. The pharmaceutical composition according to claim 4 comprising $10^6$ to $10^{12}$ cfu *Lactobacillus* per gram.

6. The pharmaceutical composition according to claim 5 in the form of a suspension, spray, gel, cream, powder, capsule, solution for lavages, ovules, a vaginal insert, tablets or a microencapsulated product.

7. The pharmaceutical composition according to claim 6 comprising up to about 10% mucous adhesive excipient.

8. The pharmaceutical composition according to claim 7, wherein the mucous adhesive excipient is a hydrocolloid.

9. The pharmaceutical composition according to claim 8, wherein the hydrocolloid is selected from the group comprising xanthan gum, locust bean or alginate.

10. The pharmaceutical composition according to claim 9, wherein the hydrocolloid is xanthan gum.

11. A preparation of *Lactobacillus* consisting of probiotic *Lactobacillus rhamnosus* strain Lbp PB01 (DSM 14870) and *Lactobacillus gasseri* strain Lba EB01 (DSM 14869).

12. The pharmaceutical composition according to claim 3, further comprising an additional probiotic *Lactobacillus* strain.

13. The pharmaceutical composition according to claim 12, wherein the additional probiotic *Lactobacillus* strain is *Lactobacillus gasseri* strain Lba EB01 (DSM 14869).

* * * * *